(12) United States Patent
Oren

(10) Patent No.: US 11,083,764 B1
(45) Date of Patent: Aug. 10, 2021

(54) PHARMACEUTICAL COMPOSITION BASED ON PLANT RAW MATERIALS

(71) Applicant: Babry Oren, Van Nuys, CA (US)

(72) Inventor: Babry Oren, Van Nuys, CA (US)

( * ) Notice: Subject to any disclaimer, the term of this patent is extended or adjusted under 35 U.S.C. 154(b) by 0 days.

(21) Appl. No.: 17/026,801

(22) Filed: Sep. 21, 2020

(51) Int. Cl.
| | |
|---|---|
| *A61K 36/906* | (2006.01) |
| *A61K 36/31* | (2006.01) |
| *A61K 36/87* | (2006.01) |
| *A61K 36/13* | (2006.01) |
| *A61K 36/15* | (2006.01) |
| *A61K 36/67* | (2006.01) |
| *A61K 9/48* | (2006.01) |
| *A61K 36/82* | (2006.01) |

(52) U.S. Cl.
CPC ............ *A61K 36/15* (2013.01); *A61K 9/48* (2013.01); *A61K 36/31* (2013.01); *A61K 36/67* (2013.01); *A61K 36/82* (2013.01); *A61K 36/87* (2013.01); *A61K 36/906* (2013.01)

(58) Field of Classification Search
None
See application file for complete search history.

(56) References Cited

FOREIGN PATENT DOCUMENTS

| | | | |
|---|---|---|---|
| CN | 101015641 A | * | 8/2007 |
| CN | 101229286 A | * | 7/2008 |
| CN | 101601732 A | * | 12/2009 |
| CN | 103461539 A | * | 12/2013 |
| CN | 103584057 A | * | 2/2014 |
| CN | 104116865 A | * | 10/2014 |
| CN | 105535511 A | * | 5/2016 |
| CN | 106509532 A | * | 3/2017 |
| CN | 107929368 A | * | 4/2018 |
| CN | 108721531 A | * | 11/2018 |
| CN | 110123886 A | * | 8/2019 |
| CN | 111166854 A | * | 5/2020 |
| IN | 201201312 I3 | * | 12/2013 |
| WO | WO2015118557 A1 | * | 8/2015 |

* cited by examiner

*Primary Examiner* — Michael Barker
*Assistant Examiner* — Randall O Winston

(57) ABSTRACT

A pharmaceutical composition containing dry powder of pine (*Pinus*) needles and dry peels and pits of grapes extract and pharmaceutically acceptable additive, dry extracts of ginger (*Zingiber officinale*), green tea (*Camellia sinensis*), yellow ginger (*Curcuma longa*), yellow mustard (*Brassica hirta*) seeds, white pepper, pomegranate (*Punica granatum*) bark and dry powder of pomegranate (*Punica granatum*) juice.

4 Claims, No Drawings

PHARMACEUTICAL COMPOSITION BASED ON PLANT RAW MATERIALS

TECHNICAL FIELD

The invention relates to the pharmaceutical industry and applies to pharmaceutical compositions made on plant raw materials, which can be used as immunomodulatory, antiviral, antibacterial, antioxidant agents, as well as for the removal of heavy metals and radionuclides from the body, including free radicals.

BACKGROUND ART

The composition for treatment of neuropathic pain caused by chemotherapy (WO 2014009936 (ABOCA SPA SOCIETA AGRICOLA) 16.01.2014), which contains polyphenols, flavonoids and anthocyanosides derived from plant raw material extracts is known. Therewith, polyphenols are derived from the extracts of yellow ginger (*Curcuma longa*) and green tea (*Camellia sinensis*), while flavonoids are derived from pomegranate (*Punica granatum*) extract.

Antimicrobial and antiviral composition (WO2004012655 (THE QUIGLEY CORP) 12.02.2004), which contains ginger (*Zingiber officinale*), green tea (*Camellia sinensis*) and yellow ginger (*Curcuma longa*) extracts is also known. This composition is preferably administered perorally and is used for the treatment of laryngitis, pharyngitis, mucositis.

Oral composition (WO2011068811 (TRIVEDI HARSH M; GITTINS ELIZABETH K) 9.06.2011), which contains ginger (*Zingiber officinale*) extract and herbal extracts, including yellow ginger (*Curcuma longa*), pomegranate (*Punica granatum*), black pepper extracts is also known. This composition has anti-inflammatory, antimicrobial, antioxidant properties and is used locally for sanation of oral cavity.

Pharmaceutical drug for treatment of mucosal disorders (WO2016198942 (MEHTA RAMAN) 15.12.2016), which contains the synergic combination of ginger (*Zingiber officinale*), yellow ginger (*Curcuma longa*) and pomegranate (*Punica granatum*) extracts is also known. This composition is used in case of viral lesions of oral cavity, lips, genital mucosa, mainly locally, in a form of a gel, dispersible tablet, buccal composition, etc. However it can also be used systemically.

Medicine for antioxidant, radioprotective, lipid metabolism regulation and treatment of cardiovascular diseases (GE5361 (Vazha Khositashvili, Levan Khositashvili, Babri Oren) 26.12.2011), which contains extract of pine (*Pinus*) needles and dry peels and pits of grapes and pharmaceutically acceptable additive, preferably sucrose is also known.

In spite of the abundance of pharmaceutical drugs based on plant raw materials, it is still important to develop herbal remedies that have a wide range of therapeutic spectrum and with ingredients have a synergic effect.

BRIEF DISCLOSURE OF THE INVENTION

One object of the invention is the pharmaceutical composition based on plant raw materials, which contains dry powder of pine (*Pinus*) needles and dry peels and pits of grapes extract and pharmaceutically acceptable additive, dry extracts of ginger (*Zingiber officinale*), green tea (*Camellia sinensis*), yellow ginger (*Curcuma longa*), yellow mustard (*Brassica hirta*) seeds, white pepper, pomegranate (*Punica granatum*) bark and dry powder of pomegranate (*Punica granatum*) juice.

In the preferable version of the invention embodiment the composition contains ingredients in the following ratio in weight % (w %):

| | |
|---|---|
| dry powder of pine needles and dry peels and pits of grapes extract and pharmaceutically acceptable additive | 25-35 |
| dry extract of ginger | 25-35 |
| dry extract of green tea | 10-18 |
| dry extract of yellow ginger | 9-16 |
| dry extract of yellow mustard seeds | 1-5 |
| dry extract of white pepper | 1-5 |
| dry extract of pomegranate bark | 1-5 |
| dry powder of pomegranate juice | 1-5 |

Another object of the invention is a medicament which contains the above mentioned composition.

In the preferable version of the invention embodiment the medicament has a form of a capsule.

In the preferable version of the invention embodiment the medicament contains the composition in amount of 320-490 mg.

FULL DISCLOSURE OF THE INVENTION

According to one object of the invention described above the pharmaceutical composition contains dry powder of pine (*Pinus*) needles and dry peels and pits of grapes extract and pharmaceutically acceptable additive, dry extracts of ginger (*Zingiber officinale*), green tea (*Camellia sinensis*), yellow ginger (*Curcuma longa*), yellow mustard (*Brassica hirta*) seeds, white pepper, pomegranate (*Punica granatum*) bark and dry powder of pomegranate (*Punica granatum*) juice.

As a result of long-term experimental studies, inventors have found that the components in the composition have a synergistic effect, namely, in terms of antiviral and immunomodulatory effects. In addition, the combination of the above components ensures effective removal of heavy metals, including lead, from the body.

The composition is prepared as follows: initially, the components included in the composition are prepared separately. Extract of pine needles and dry peels and pits of grapes is prepared according to the method described in Georgian Patent GE5361. Liquid pharmaceutically acceptable additive is added to the obtained extract. The extract and the pharmaceutically acceptable additive are mixed in the same ratio as described in Georgian Patent GE5361. Finally obtained mixture is dried till making a dry powder. Drying is possible by any method known in the pharmaceutical industry, preferably spray drying is used. Extracts of ginger, green tea, yellow ginger, yellow mustard seeds, white pepper and pomegranate bark are prepared separately. Extracts are prepared by any technology known in the pharmaceutical industry. Obtained liquid extracts are dried separately. Drying is possible by any method known in the pharmaceutical industry, preferably spray drying is used. Finally dry extracts are obtained. Pomegranate juice is obtained by any known technology, preferably by pressing. Obtained juice is dried. Drying is possible by any method known in the pharmaceutical industry, preferably spray drying is used. Finally dry powder is obtained. Powders obtained separately by the method described above are mixed till making homogeneous mass. In the preferable version of the invention embodiment the components are mixed in such

| a ratio that the finally obtained composition contains ingredients in the following ratio in w %: | |
| --- | --- |
| dry powder of pine needles and dry peels and pits of grapes extract and pharmaceutically acceptable additive | 25-35 |
| dry extract of ginger | 25-35 |
| dry extract of green tea | 10-18 |
| dry extract of yellow ginger | 9-16 |
| dry extract of yellow mustard seeds | 1-5 |
| dry extract of white pepper | 1-5 |
| dry extract of pomegranate bark | 1-5 |
| dry powder of pomegranate juice | 1-5 |

In preferable version of the embodiment of another object of the invention —medicament, the latter has a form of a capsule. The capsules are filled with the above mentioned composition, by the method well-known in the pharmaceutical industry. In preferable version of the invention embodiment the capsule contains the composition in amount of 320-480 mg.

Indications for using the medicament are as follows: treatment and prophylaxis of impaired immune conditions, bacterial and viral infections, inflammatory conditions, as well as removal of heavy metals and radionuclides from the body, reducing the amount of free radicals in the body.

Dosage of the medicament (preferably capsule) is 320-480 mg (one capsule) 2-3 times per day. Peroral administration of the medicament is possible, though it is better to dissolve the powder contained in the medicament (for example a capsule) in 32° C. boiled water and take it orally in a form of liquid. The medicament is administered 15-30 minutes before eating.

SPECIFIC EXAMPLES OF CARRYING OUT OF THE INVENTION

Example 1

| The composition contains the components in the following ratio in mg: | |
| --- | --- |
| dry powder of pine needles and dry peels and pits of grapes extract and pharmaceutically acceptable additive | 120 |
| dry extract of ginger | 120 |
| dry extract of green tea | 40 |
| dry extract of yellow ginger | 60 |
| dry extract of yellow mustard seeds | 12 |
| dry extract of white pepper | 16 |
| dry extract of pomegranate bark | 16 |
| dry powder of pomegranate juice | 16 |
| Total weight of the composition | 400 mg |

Example 2

| The composition contains the components in the following ratio in mg; | |
| --- | --- |
| dry powder of pine needles and dry peels and pits of grapes extract and pharmaceutically acceptable additive | 80 |
| dry extract of ginger | 80 |
| dry extract of green tea | 48 |
| dry extract of yellow ginger | 48 |
| dry extract of yellow mustard seeds | 16 |
| dry extract of white pepper | 16 |
| dry extract of pomegranate bark | 16 |
| dry powder of pomegranate juice | 16 |
| Total weight of the composition | 320∂ₐ |

Example 3

| The composition contains the components in the following ratio in mg: | |
| --- | --- |
| dry powder of pine needles and dry peels and pits of grapes extract and pharmaceutically acceptable additive | 171.5 |
| dry extract of ginger | 171.5 |
| dry extract of green tea | 49 |
| dry extract of yellow ginger | 78.4 |
| dry extract of yellow mustard seeds | 4.9 |
| dry extract of white pepper | 4.9 |
| dry extract of pomegranate bark | 4.9 |
| dry powder of pomegranate juice | 4.9 |
| Total weight of the composition | 490 mg |

A number of researches have been carried out to study the effectiveness of the proposed by the invention composition.

In Vivo Study of Anti-Inflammatory Effect

BALB/c mice were divided into groups, with 10 mice in each of them. The first group was given an aqueous solution of dry powder of pine needles and dry peels and pits of grapes extract and pharmaceutically acceptable additive, with 5 mg/kg dosage of an active ingredient. The second group was given an aqueous solution of mixture of dry extracts of ginger, yellow ginger and pomegranate, with 5 mg/kg dosage of an active ingredient. The third group was given an aqueous solution of the composition described in example 1, with 5 mg/kg dosage of an active ingredient. In one hour after administration, all groups were intraperitoneally injected with lipopolysaccharide (LPS), dissolved in sterile, apirogenic saline with a dose of 1 mg/kg. The negative control group was receiving saline solution in a form of intraperitoneal injection. Rolipram (30 mg/kg, perorally) was used as standard pharmaceutical drug. After an hour, blood was drawn from the abdominal artery. Heparin (5 µl) was used as an anticoagulant in tubes filled with collected blood. Plasma was removed from the blood by centrifugation at room temperature, was divided into aliquots and stored at −70° C. temperature until analysis. TNF-α levels were tested in blood samples by ELISA and the percentage of inhibition of TNF-α release compared to the control group was determined. The obtained results are shown in Table 1.

TABLE 1

| Group Number | Inhibition % |
| --- | --- |
| 1 | 28.38 ± 7.34 |
| 2 | 43.68 ± 5.14 |
| 3 | 93.2 ± 3.65 |

Study of Antibacterial Effect

Patients suffering of bacterial infection of the oral cavity were divided into 4 groups of three patients. The first group was given an aqueous solution of dry powder of pine needles and dry peels and pits of grapes extract and pharmaceutically acceptable additive to gargle (320 mg dry powder was dissolved in 150 ml water). The second group was given an aqueous solution of mixture of ginger, yellow ginger and pomegranate dry extracts to gargle three times per day (320 mg dry powder was dissolved in 150 ml water). The third group was given an aqueous solution of the composition described in example 2, to gargle three times per day (320 mg dry powder was dissolved in 150 ml water). The fourth group was a control one and was given placebo. One hour before starting the treatment and one hour after the last treatment with aqueous solutions the patients gargled for 30 sec with physiological solution. After that, 0.5 ml of each gargled physiological solution were cultivated on agar for 36 hours, in lab standard conditions, after this the number of bacteria was counted. The obtained average data are shown in Table 2.

TABLE 2

| Group Number | Bacterial Count ($\times 10^5$) | |
| --- | --- | --- |
| | before treatment | after treatment |
| 1 | 46 | 39.8 |
| 2 | 40.6 | 6.5 |
| 3 | 41.5 | 5.6 |
| 4 | 43 | 44.5 |

In Vitro Study of Antioxidant Effect

Three samples were examined to evaluate antioxidant effectiveness. The first sample was the aqueous solution of the composition described in Example 1; the second sample was the aqueous solution of a mixture of ginger, yellow ginger and pomegranate dry extracts; the third sample was the solution of pine needles and dry peels and pits of grapes extract and sucrose (medicine described in Georgian Patent GE5362); the fourth sample was control—Ethylenediaminetetraacetate.

Method: Evaluation was done by determining the intermediate product of the lipid oxidation process, malondialdehyde (MDA). Amount of MDA increases under the influence of ferrous sulfate (FeSO4), this moment was used as a model for the activated oxidation process.

Sequence of analysis: 0.3 ml of blood serum was added to 0.1 ml of test sample, 1 μmol of ferrous sulfate solution and incubated at 37° C. for 15 min. Then 3 ml of 3% orthophosphoric acid and 1 ml of 0.6% thiobaric acid were added to the incubation mixture. The mixture was placed on a boiling water bath for one hour. Then 4 ml of butanol was added. The obtained mixture was centrifuged for 10 minutes at 3000 rpm. In the obtained supernatant, the optical density (E) was determined on a spectrometer on a wavelength of 535 nm. MDA concentration (C) was determined by the formula $C = E \times 84.5$ μmol/L. The difference between the background concentration of MDA and iron activated was 100%, while the antioxidant activity of the samples was conditionally expressed in %. The obtained results are shown in Table 3.

TABLE 3

| Sample Number | Relative Antioxidant Activity in % |
| --- | --- |
| 1 | 176 |
| 2 | 99 |
| 3 | 157 |
| 4 | 92 |

In Vivo Study of the Effectiveness of Removing Heavy Metals from the Body

The study was conducted on children with econephropathies who were from regions contaminated with heavy metal salts. The children were given the medicine offered by the invention, namely, a 320 mg capsule three times per day during seven days. Urinary excretion of heavy metals before and during the treatment was investigated to evaluate the effectiveness of the medicine. The results of the study are shown in Table 4.

TABLE 4

| Heavy Metal | Excretion Before Treatment mcg/l | Excretion During Treatment mcg/l |
| --- | --- | --- |
| Arsenic | 1.1 | 12.1 |
| Chromium | 1.4 | 3.6 |
| Cadmium | 0.01 | 0.02 |
| Lead | 0.1 | 1.8 |

Study of Radioprotective Effect

White rats (*Rattus*) were used for the study. A model of acute radiation sickness was created with single, total, equal irradiation of animals. The animals were divided into 8 groups with 10 animals in each. Four groups of animals were irradiated with a dose of 8 Gy, which causes death of bone marrow. The remaining four groups of animals were irradiated with a dose of 10 Gy, which causes irreversible damage to the gastrointestinal tract.

Irradiation of animals in the first four groups with a dose of 8 Gy was performed according to the following scheme: Group 1 (control): only irradiation; Group 2: the aqueous solution of the composition described in Example 3, with a dose of 7 mg/kg of an active ingredient, 3 times per day, for 5 days and then irradiation; Group 3: irradiation and then the aqueous solution of the composition described in Example 3, with a dose of 7 mg/kg of an active ingredient, 3 times per day, till the death of an animal or for 15 days; Group 4: the aqueous solution of the composition described in Example 3, with a dose of 7 mg/kg of an active ingredient, 3 times per day, for 5 days, then irradiation and then the aqueous solution of the composition described in Example 3, with a dose of 7 mg/kg of an active ingredient, 3 times per day, till the death of an animal or for 15 days.

Irradiation of animals in the second four groups with a dose of 10 Gy was performed according to the following scheme: Group 5 (control): only irradiation; Group 6: the aqueous solution of the composition described in Example 3, with a dose of 7 mg/kg of an active ingredient, 3 times per day, for 5 days and then irradiation; Group 7: irradiation and then the aqueous solution of the composition described in Example 3, with a dose of 7 mg/kg of an active ingredient, 3 times per day, till the death of an animal or for 15 days; Group 8: the aqueous solution of the composition described in Example 3, with a dose of 7 mg/kg of an active ingredient, 3 times per day, for 5 days, then irradiation and then the aqueous solution of the composition described in Example 3, with a dose of 7 mg/kg of an active ingredient, 3 times per day, till the death of an animal or for 15 days. The average life expectancy of each group of animals and the percentage of survived animals in the group were determined during the experiment. The results of the study are shown in Table 5.

TABLE 5

| Group No | Average Life Expectancy (days) | Number of Survived Animals |
|---|---|---|
| 1 | 10 | 0 |
| 2 | 15 | 1 (10%) |
| 3 | 14 | 1 (10%) |
| 4 | 20 | 2 (20%) |
| 5 | 5 | 0 |
| 6 | 10 | 0 |
| 7 | 8 | 0 |
| 8 | 12 | 1 (10%) |

Study of Immunomodulatory Activity

1. Study of Blast Transformation of Lymphocytes

Research was carried out to study the effect of herbal extracts on cell immunity. In vitro blast transformation or blastogenesis of normal lymphocytes was used to assess the above mentioned. Blastogenesis is the initial step in the induction of cell immunity and is associated with the secretion of various interleukins which are essential for intercellular interaction of the immune system.

The study was carried out on three samples. The first sample was the aqueous solution of the composition described in Example 1, at a concentration of 4 mg/ml; the second sample was the aqueous solution of a mixture of ginger, yellow ginger and pomegranate dry extracts at a concentration of 4 mg/ml; the third sample was the aqueous solution of dry powder of pine needles and dry peels and pits of grapes extract and sucrose at a concentration of 4 mg/ml.

Blast transformation was measured via a conventional lymphocyte stimulation test wherein $^3$H-thymidine was added to lymphocyte suspension, followed by incubation, cell harvesting and measuring radioactivity of the harvested cells. A high radioactivity count indicates that the lymphocytes have undergone transformation and taken up the $^3$H-thymidine.

Lymphocytes were obtained from the blood of healthy people by separation via density gradient method in Ficoll Isopaque. Multi-well plates were prepared containing lymphocyte suspensions in Hanks solution supplemented with 10% fetal calf serum, penicillin and streptomycin. The first sample was added to the wells of the first plate, 20 µl to each well, the second sample was added to the wells of the second plate, 20 µl to each well and the third sample was added to the wells of the third plate, 20 µl to each well. One more plate was used for control and nothing was added to its wells. The final volume of lymphocyte suspension in each well was 0, 2 ml. The plates were then incubated for 72 hours at 37° C. in a $CO_2$ incubator. To each well 0.05 ml of $^3$H-thymidine was added after incubation, followed by a further 24 hours of incubation at 37° C. Then the cells were harvested with an automatic harvester, and radioactivity was measured with a scintillation counter. The obtained results are shown in Table 6.

TABLE 6

| Sample | Average Count of $^3$H-thymidine Uptake | Stimulation Index |
|---|---|---|
| Control | 284 counts/min | 0 |
| Sample 1 | 895 counts/min | 3.15 |
| Sample 2 | 672 counts/min | 2.37 |
| Sample 3 | 364 counts/min | 1.28 |

The results show that the composition of the invention significantly increases cell immunity by stimulating blastogenesis, which finally boosts secretion of cytokines.

2. Study of Stimulation of Cytokine Production

Research was carried out to study the stimulation of cytokines production by herbal extracts. The study was carried out on three samples. The first sample was the aqueous solution of the composition described in Example 1, at a concentration of 10%; the second sample was the aqueous solution of a mixture of ginger, yellow ginger and pomegranate dry extracts, at a concentration of 10%; the third sample was the aqueous solution of dry powder of pine needles and dry peels and pits of grapes extract and sucrose at a concentration of 10%.

The effect of the samples, on cytokine production in peripheral mononuclear blood cells of healthy people, was measured using the method described in the following documents: D. Schols and E. De Clencq, Human Immunodeficiency Virus Type gp120 Induces Anergy In Human Peripheral Blood Lynphocytes By Inducing Interleukin Production, J. Virol., 1996, Vol. 70, p. 4953-4960. The obtained results are shown in Table 7.

TABLE 7

| Sample | IL-2 (pg/ml) | IL-4 (pg/ml) | IL-10 (pg/ml) | IFN-γ (pg/ml) |
|---|---|---|---|---|
| Control | insignificant | not detected | 35 | 31 |
| Sample 1 | 68 | not detected | 711 | 286 |
| Sample 2 | 48 | not detected | 502 | 197 |
| Sample 3 | 27 | not detected | 282 | 112 |

The obtained results demonstrate that the composition of the invention significantly boosts cytokine production in peripheral mononuclear blood cells of people.

Study on Antiviral Activity

1. In Vitro Study of Antiviral Activity Against Herpes Simplex Virus Type 2

The antiviral activity of three samples against the second type of herpes simplex virus was studied. The first sample was the aqueous solution of the composition described in Example 1, at a concentration of 4 mg/ml; the second sample was the aqueous solution of a mixture of ginger, yellow ginger and pomegranate dry extracts, at a concentration of 4 mg/ml; the third sample was the aqueous solution of pine needles and dry peels and pits of grapes extract and sucrose dry powder, at a concentration of 4 mg/ml.

For the study Vero cells (renal cells from monkey) were used. The cells were cultivated in the $CO_2$-thermostat at 37° C. temperature, on plates with the medium of RPMI-1640+ fetal serum (Nuclon, Surface, Denmark). For studying antiviral activity the one day and night cultures of Vero cells with confluent cell monolayer were used. Growth medium was removed, experimental samples were applied on the cell monolayer. In one hour after the application, the second type of herpes simplex virus (HSV) in dose of 100 $TCD_{50}$ ($TCD_{50}$ is Tissue cytopathogenic dose of the virus, which causes damage to 50% of cell monolayer) was added and the supporting medium was placed into the wells (serum-free nutritive medium).

Cultures were incubated in $CO_2$-thermostat during 3 days, with daily microscopic control and registration of viral reproduction which was expressed by HSV cytopathic effect on Vero cells in comparison with control culture, where the monolayer was not treated with experimental samples.

An HSV cytopathic effect is morphologically expressed as formation of symplasts or round cells along with proliferation and creation of giant multinuclear cells.

After three days, cultures were collected from the plate wells and the infectious titers for each experimental sample were determined. HSV reproduction titers are shown in Table 8.

TABLE 8

| Sample | Indections Titer lg $TCD_{50}$ |
|---|---|
| Sample 1 | 2.0 |
| Sample 2 | 4.0 |
| Sample 3 | 5.0 |
| Control | 7.0 |

The results provided in the Table show that the composition of the invention has the ability to dramatically suppress the second type of herpes simplex virus.

2. In Vitro Study of Anti-Influenza Activity

The antiviral activity of three samples against the influenza virus (H1N1) was studied. The first sample was the aqueous solution of the composition described in Example 1, at a concentration of 4 mg/ml; the second sample was the aqueous solution of a mixture of ginger, yellow ginger and pomegranate dry extracts, at a concentration of 4 mg/ml; the third sample was the aqueous solution of pine needles and dry peels and pits of grapes extract and sucrose dry powder, at a concentration of 4 mg/ml.

For the study MDCK cells (renal cells from dog) were used. The cells were cultivated in the $CO_2$-thermostat at 37° C. temperature, on plates with the medium of RPMI-1640+ fetal serum (Nuclon, Surface, Denmark). For enhance of cell sensitivity to contamination with the influenza virus, the processing with trypsin was performed. For studying antiviral activity the one day and night cultures of MDCK cells with confluent cell monolayer were used. Growth medium was removed, experimental samples were applied on the cell monolayer. In one hour after the application of the samples, the influenza virus was added and the supporting medium was placed into the wells (serum-free nutritive medium).

Cultures were incubated in $CO_2$-thermostat during 3 days, with daily microscopic control and registration of viral reproduction which was expressed by cytopathic effect of the influenza virus on MDCK cells in comparison with control culture, where the monolayer was not treated with experimental samples.

After three days, cultures were collected from the plate wells and the infectious titers for each experimental sample were determined. Reproduction titers of the influenza virus are shown in Table 9.

TABLE 9

| Sample | Infectious Titer lg $TCD_{50}$ |
|---|---|
| Sample 1 | 2.0 |
| Sample 2 | 4.0 |
| Sample 3 | 5.0 |
| Control | 6.0 |

The results provided in the Table show that the composition of the invention has the ability to dramatically suppress the influenza virus.

3. Study of Antiviral Activity Against Herpes Virus

The antiviral activity of three samples against the herpes virus was studied. The first sample was the aqueous solution of the composition described in Example 1, at a concentration of 4 mg/ml; the second sample was the aqueous solution of a mixture of ginger, yellow ginger and pomegranate dry extracts, at a concentration of 4 mg/ml; the third sample was the aqueous solution of pine needles and dry peels and pits of grapes extract and sucrose dry powder, at a concentration of 4 mg/ml.

During the research as a form of the virus was used the virus isolated from the blood serum of a person with herpetic infection. The virus-containing material was a culture fluid which was taken from the swine embryo kidney cell cultures infected with the virus isolated by the method mentioned above, at the peak of cytopathic manifestation. For the research the virus in dose of 10 $TCD_{50}$ was used.

The swine embryo kidney cells, cultivated in the form of single-day monolayer in 24-slot plates on medium 199, with addition of 7% cattle serum, 100 IU/mi penicillin and 100 IU/ml streptomycin were used for the study.

Experimental samples were applied on the monolayer of the cells; then viability and proliferative activity of cells were observed over 4 days. The results were determined according to the percentage of viable cells and their proliferative activity. The results of the study are shown in Table 10.

TABLE 10

| Sample | dead cells % in monolayer |
|---|---|
| Sample 1 | 25% |
| Sample 2 | 55% |
| Sample 3 | 70% |
| Control | 100% |

The results provided in the Table show that the composition of the invention has sharply expressed antiviral activity against the herpes virus.

The invention claimed is:

1. A pharmaceutical composition comprising a dry powder of pine needles and dry peels pits of grapes extract and pharmaceutically acceptable additive, a dry extract of ginger, a dry extract of green tea, a dry extract of yellow ginger, a dry extract of yellow mustard seeds, a dry extract of white pepper, a dry extract of pomegranate bark, a dry powder of pomegranate juice and wherein said composition is in the following ratio in weight percentages:

| | |
|---|---|
| dry powder of pine needles and dry peels pits of grapes extract and pharmaceutically acceptable additive | 25-35 |
| dry extract of ginger | 25-35 |
| dry extract of green tea | 10-18 |
| dry extract of yellow ginger | 9-16 |
| dry extract of yellow mustard seeds | 1-5 |
| dry extract of white pepper | 1-5 |
| dry extract of pomegranate bark | 1-5 |
| dry powder of pomegranate juice | 1-5. |

2. A medicament comprising the composition according to claim 1.

3. The medicament according to claim 2 in the form of a capsule.

4. The medicament according to claim 2 wherein the composition is in an amount of 320-480 mg.

* * * * *